(12) United States Patent
Cunningham et al.

(10) Patent No.: US 11,607,280 B2
(45) Date of Patent: *Mar. 21, 2023

(54) APPARATUS AND METHOD FOR USING A REMOTE CONTROL SYSTEM IN SURGICAL PROCEDURES

(71) Applicant: Covidien LP, Mansfield, MA (US)

(72) Inventors: James S. Cunningham, Boulder, CO (US); Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 477 days.

This patent is subject to a terminal disclaimer.

(21) Appl. No.: 16/792,201

(22) Filed: Feb. 15, 2020

(65) Prior Publication Data
US 2020/0197114 A1   Jun. 25, 2020

Related U.S. Application Data

(63) Continuation of application No. 15/420,390, filed on Jan. 31, 2017, now Pat. No. 10,561,468, which is a continuation of application No. 13/205,889, filed on Aug. 9, 2011, now Pat. No. 9,554,866.

(51) Int. Cl.
| | |
|---|---|
| *A61B 18/12* | (2006.01) |
| *A61B 34/30* | (2016.01) |
| *A61B 34/00* | (2016.01) |
| *A61B 90/00* | (2016.01) |

(Continued)

(52) U.S. Cl.
CPC .............. *A61B 34/30* (2016.02); *A61B 18/14* (2013.01); *A61B 34/76* (2016.02); *A61B 90/03* (2016.02); *A61B 18/1445* (2013.01); *A61B 2017/00119* (2013.01); *A61B 2017/00207* (2013.01);

(Continued)

(58) Field of Classification Search
CPC ...... A61B 18/1445; A61B 34/00; A61B 34/30
See application file for complete search history.

(56) References Cited

U.S. PATENT DOCUMENTS

| | | | |
|---|---|---|---|
| 5,279,309 A | 1/1994 | Taylor et al. |
| 5,368,032 A | 11/1994 | Cline et al. |
| 5,784,542 A | 7/1998 | Ohm et al. |

(Continued)

FOREIGN PATENT DOCUMENTS

WO   0101847 A1   1/2001

*Primary Examiner* — Daniel W Fowler
(74) *Attorney, Agent, or Firm* — Carter, DeLuca & Farrell LLP

(57) ABSTRACT

A system and method for using a remote control to control an electrosurgical instrument, where the remote control includes at least one momentum sensor. As the surgeon rotates their hand mimicking movements of a handheld electrosurgical instrument, the movements are translated and sent to the remote controlled (RC) electrosurgical instrument. The surgeon uses an augmented reality (AR) vision system to assist the surgeon in viewing the surgical site. Additionally, the surgeon can teach other doctors how to perform the surgery by sending haptic feedback to slave controllers. Also, the surgeon can transfer control back and forth between the master and slave controller to allow a learning surgeon to perform the surgery, but still allow the surgeon to gain control of the surgery whenever needed. Also, the surgeon could be located at a remote location and perform the surgery with the assistance of the AR vision system.

13 Claims, 11 Drawing Sheets

(51) Int. Cl.
*A61B 18/14* (2006.01)
*A61B 17/00* (2006.01)

(52) U.S. Cl.
CPC ............ *A61B 2017/00212* (2013.01); *A61B 2017/00221* (2013.01); *A61B 2090/365* (2016.02)

(56) References Cited

U.S. PATENT DOCUMENTS

| | | |
|---|---|---|
| 5,791,231 A | 8/1998 | Cohn et al. |
| 5,795,295 A | 8/1998 | Hellmuth et al. |
| 5,876,325 A | 3/1999 | Mizuno et al. |
| 6,106,511 A | 8/2000 | Jensen |
| 6,223,100 B1 | 4/2001 | Green |
| 6,690,960 B2 | 2/2004 | Chen et al. |
| 6,837,883 B2 | 1/2005 | Moll et al. |
| 6,846,307 B2 | 1/2005 | Whitman et al. |
| 7,542,791 B2 | 6/2009 | Mire et al. |
| 7,892,243 B2 | 2/2011 | Stuart |
| 8,202,244 B2 | 6/2012 | Cohen et al. |
| 9,554,866 B2 | 1/2017 | Cunningham et al. |
| 10,561,468 B2 | 2/2020 | Cunningham et al. |
| 2002/0156466 A1* | 10/2002 | Sakurai ............... A61B 1/00016 606/1 |
| 2003/0208189 A1 | 11/2003 | Payman |
| 2004/0128026 A1 | 7/2004 | Harris et al. |
| 2004/0152972 A1 | 8/2004 | Hunter |
| 2005/0004559 A1 | 1/2005 | Quick |
| 2006/0058616 A1 | 3/2006 | Marquart et al. |
| 2006/0178559 A1 | 8/2006 | Kumar et al. |
| 2007/0106306 A1 | 5/2007 | Bodduluri et al. |
| 2007/0167845 A1 | 7/2007 | Sasagawa et al. |
| 2008/0243064 A1 | 10/2008 | Stabler et al. |
| 2009/0036902 A1 | 2/2009 | DiMaio et al. |
| 2009/0062814 A1 | 3/2009 | Omori |
| 2009/0287351 A1 | 11/2009 | Howison et al. |
| 2010/0125266 A1* | 5/2010 | Deem ............ A61B 17/320036 606/192 |
| 2010/0217991 A1* | 8/2010 | Choi ..................... G16H 20/40 380/255 |
| 2010/0228249 A1 | 9/2010 | Mohr et al. |
| 2011/0195647 A1 | 8/2011 | Schill et al. |

\* cited by examiner

APPARATUS AND METHOD FOR USING A REMOTE CONTROL SYSTEM IN SURGICAL PROCEDURES

CROSS-REFERENCE TO RELATED APPLICATIONS

This is a continuation of and claims priority to U.S. patent application Ser. No. 15/420,390, filed Jan. 31, 2017, which is a continuation of and claims priority to U.S. patent application Ser. No. 13/205,889, filed Aug. 9, 2011, now U.S. Pat. No. 9,554,866, the entire contents of each of which are hereby incorporated by reference.

BACKGROUND

Technical Field

The present disclosure relates to a system and method for remotely controlling an electrosurgical instrument and, more particularly, to a remote control that uses momentum sensors to allow the surgeon to rotate and/or move the remote in a similar manner to handheld electrosurgical instrument.

Background of Related Art

Minimally invasive surgical procedures typically employ small incisions in body cavities for access of various surgical instruments, including forceps, laparoscopes, scalpels, scissors, and the like. It is often the case that several surgical hands, such as several laparoscopic instrument and camera holders, are necessary to hold these instruments for the operating surgeon during the particular surgical procedure. With the introduction of robotic-assisted minimally invasive surgery (MIS) in recent years, hospitals worldwide have made significant inves Intents in acquiring this latest technology for their respective facilities.

Thus, it is known to use robotic-assisted MIS when carrying out surgical operations. When surgery of this kind is performed, access to a subcutaneous surgical site is provided via a number (typically 3 to 5) of small (typically 5-12 mm) incisions, through which a surgical arm is manually passed. The surgical arms are then coupled to the surgical robotic instrument, which is capable of manipulating the surgical arms for performing the surgical operations, such as suturing or thermally cutting through tissue and cauterizing blood vessels that have been severed. The surgical arms thus extend through the incisions during the surgery, one of which incisions is used for supplying a gas, in particular carbon dioxide, for inflating the subcutaneous area and thus create free space at that location for manipulating the surgical instruments.

Therefore, open surgeries often require a surgeon to make sizable incisions to a patient's body in order to have adequate visual and physical access to the site requiring treatment. The application of laparoscopy for performing procedures is commonplace. Laparoscopic surgeries are performed using small incisions in the abdominal wall and inserting a small endoscope into the abdominal cavity and transmitting the images captured by the endoscope onto a visual display. The surgeon may thus see the abdominal cavity without making a sizable incision in the patient's body, reducing invasiveness and providing patients with the benefits of reduced trauma, shortened recovery times, and improved cosmetic results. In addition to the endoscope, laparoscopic surgeries are performed using long, rigid tools inserted through incisions in the abdominal wall.

However, conventional techniques and tools for performing laparoscopic procedures may limit the dexterity and vision of the surgeon. Given the size of the incisions, the maneuverability of the tools is limited and additional incisions may be required if an auxiliary view of the surgical site is needed. Thus, robotic instruments may be used to perform laparoscopic procedures.

One example of a robotic assisted MIS system is the da Vinci® System that includes an ergonomically designed surgeon's console, a patient cart with four interactive robotic arms, a high performance vision system, and instruments. The da Vinci it console allows the surgeon to sit while viewing a highly magnified 3D image of the patient's interior sent from the high performance vision system. The surgeon uses master controls on the console that work like forceps to perform the surgery. The da Vinci® system corresponds to the surgeon's hand, wrist, and finger movements into precise movements of the instruments within the patient's interior.

However, the da Vinci® system only allows a single user to use the console and controllers at one time. Additionally, the 3D image shown in the da Vinci® system can only be viewed by the surgeon sitting at the console which prevents other surgeon's from assisting the surgeon in determining the best procedure to perform the surgery or from showing students how to perform the surgery. Additionally, the da Vinci® system is large and cumbersome and oversized relative to the electrosurgical instruments used in the procedure.

SUMMARY

In accordance with the present disclosure, a system and method for using a remote control to control an electrosurgical instrument, where the remote control includes at least one momentum sensor. As the surgeon rotates their hand mimicking movements of a handheld electrosurgical instrument, the movements are translated and sent to the remote controlled (RC) electrosurgical instrument. The surgeon uses an augmented reality (AR) vision system to assist the surgeon in viewing the surgical site. Additionally, the surgeon can teach other doctors/students how to perform the surgery by sending haptic feedback to slave controllers. Also, the surgeon can transfer control back and forth between the master and slave controllers to teach another surgeon how to perform the surgery, but still allow the teaching surgeon to gain control of the surgery whenever needed. Also, the teaching surgeon could be located at a remote location and perform the surgery with the assistance of the AR vision system.

According to an embodiment of the present disclosure, a method for performing an electrosurgical procedure includes the steps of generating a pre-operative image of an anatomical section of a patient and analyzing the pre-operative image to generate data about the anatomical section of the patient to assist a user during surgery. The method also includes the steps of receiving a real time video signal of a surgical site within the patient and displaying on a user interface the analyzed data with the video signal. Further, the method includes the step of inserting a remote controlled electrosurgical instrument within the patient. The remote controlled electrosurgical instrument is configured to communicate with a remote. Additionally, the method includes the steps of moving, rotating, and/or selecting a button on the remote in a similar manner to a hand-held electrosurgical instrument while the user uses the user interface to view the surgical site, and moving, rotating, and/or performing other actions by the remote controlled surgical instrument based on movements and or actions of the remote.

According to another embodiment of the present disclosure, a method for performing an electrosurgical procedure includes the step of inserting a remote controlled electrosurgical instrument within a patient. The remote controlled electrosurgical instrument with at least one sensor and a base. The method further includes the step of moving a remote in a manner substantially similar to movement of a handheld electrosurgical instrument. The remote is configured with at least one momentum sensor. Also, the method includes the step of sending information from the momentum sensor to the base to move the remote controlled electrosurgical instrument within the patient based on movements of the remote.

According to another embodiment of the present disclosure, a system for performing an electrosurgical procedure includes a remote controlled electrosurgical instrument configured to be inserted within a patient. The remote controlled electrosurgical instrument includes a base and the base connects to a remote. The remote is configured with at least one momentum sensor and at least one switch. The remote controlled electrosurgical instrument responds to twists, rotation, side to side, up and down, diagonal, and other motions of the remote as a user moves the remote in a similar manner to a handheld electrosurgical instrument.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
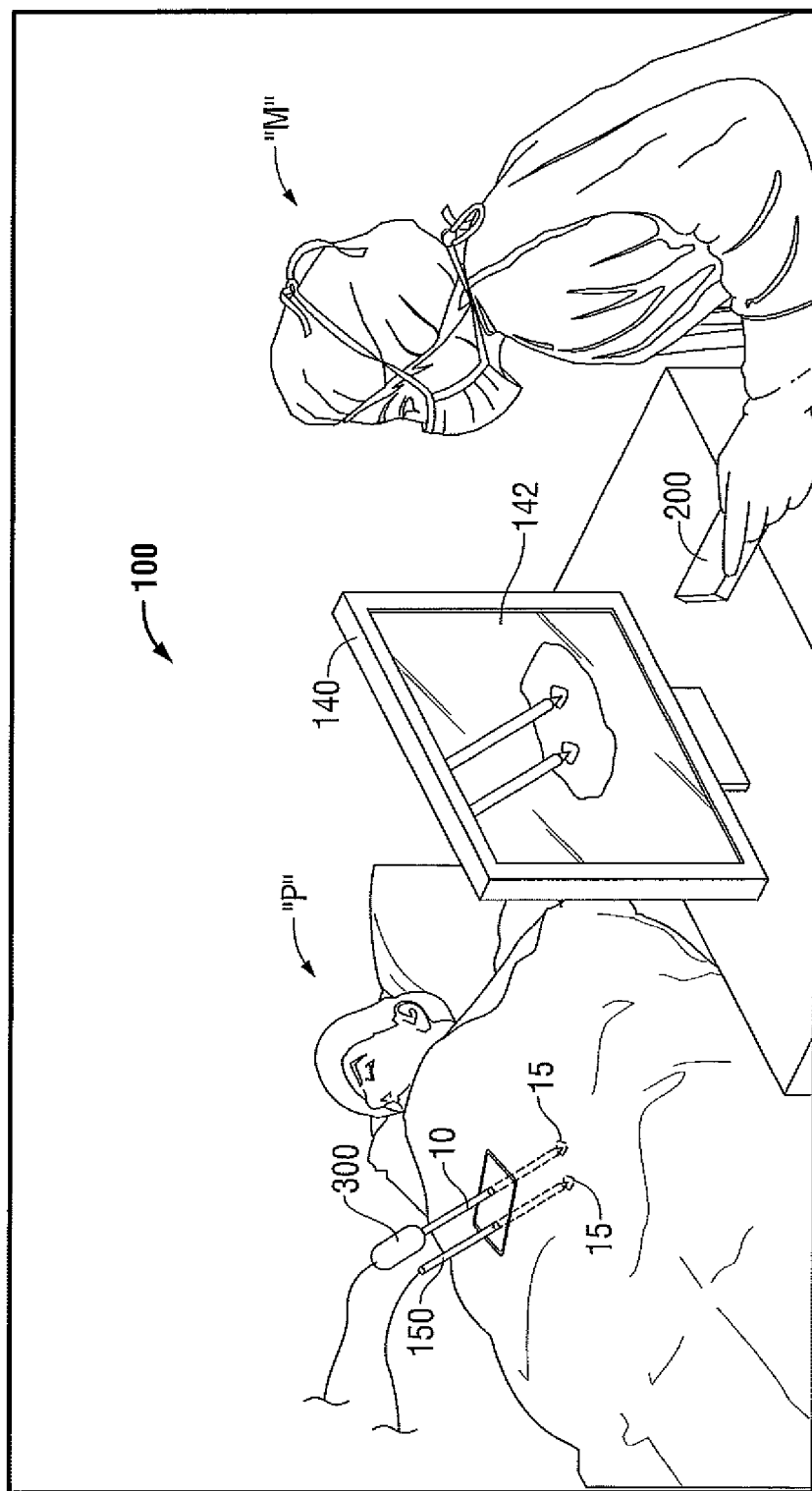
FIG. 1 is a schematic diagram of a remote controlled surgical system in accordance with an embodiment of the present disclosure.

FIG. 1 is a schematic diagram of a remote controlled surgical system 100 that allows a surgeon M to perform a surgical procedure on patient P using a remote 200. Access to a subcutaneous surgical site within patient P is provided via a number (typically 3 to 5) of small (typically 5-12 mm) incisions 15, through which at least one remote controlled (RC) electrosurgical instrument 10 is manually passed. Additionally, a camera 150 is inserted in at least one incision 15 to give the surgeon M a view of the surgical site. The video signal from the camera may be sent to an Augmented Reality (AR) controller 600 (See FIGS. 5 and 6) to add additional data. The video signal and additional data are then displayed on a user interface 140. The AR displayed image 142 may include labels on instruments, labels and/or margins of organs, tumors, or other anatomical bodies, and/or boundary zones around delicate anatomical bodies. The AR displayed image 142 may be in 2D or 3D. As the camera 150 is moved around the surgical site, the labels and data overlaid onto the video image move to the appropriate location.

The surgeon M controls the RC electrosurgical instrument 10 by rotating and/or moving the remote 200 up, down, left, right, diagonally, and/or rotating. The movement of the remote 200 may be configured to move in a manner similar to a hand-held electrosurgical instrument. Additionally, the surgeon M can press a button on the remote 200 to activate an electrical signal to coagulate or cut tissue, staple tissue, or perform another function of the instrument. The surgeon M can be located in the same room as a patient or in a remote location such as another state or country. The remote 200 may be configured to send data to a base 300 attached to the RC electrosurgical instrument 10. The data may be sent to the base 300 through a direct electrical connection or by Bluetooth®, ANT3®, KNX®, ZWave®, X10® Wireless USB®, IrDA®, Nanonet, Tiny OS®, ZigBee®, 802.11 IEEE, and other radio, infrared, UHF, VHF communications and the like.

Figure 2A:
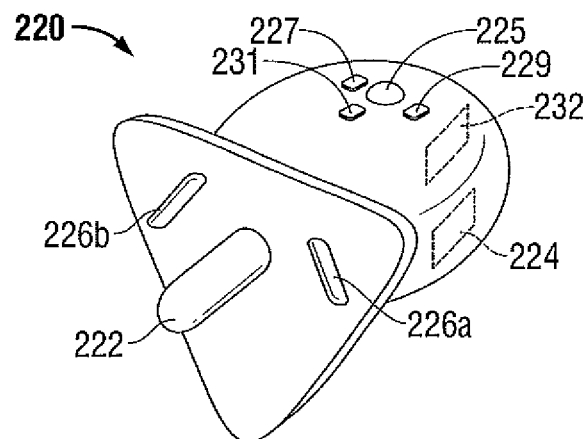
FIGS. 2A-C are perspective views of different remotes used in accordance with an embodiment of the present disclosure.
Figure 2B:
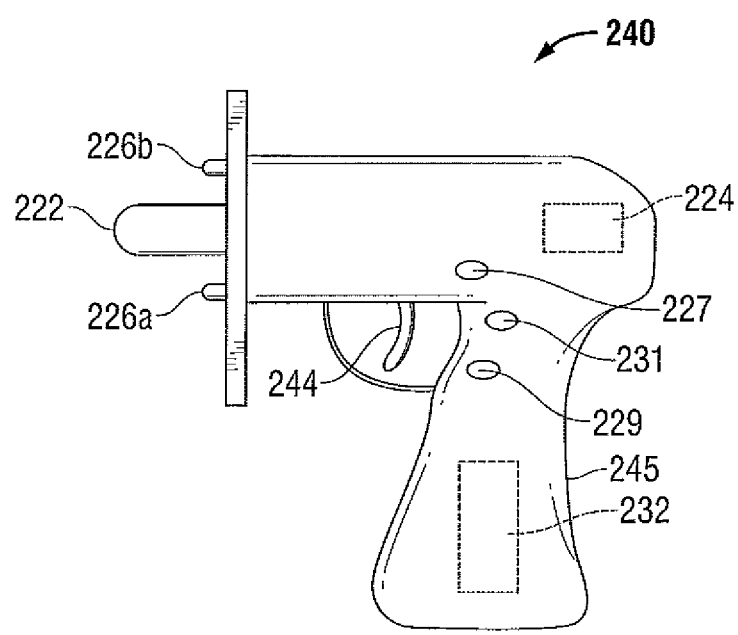
Figure 2C:
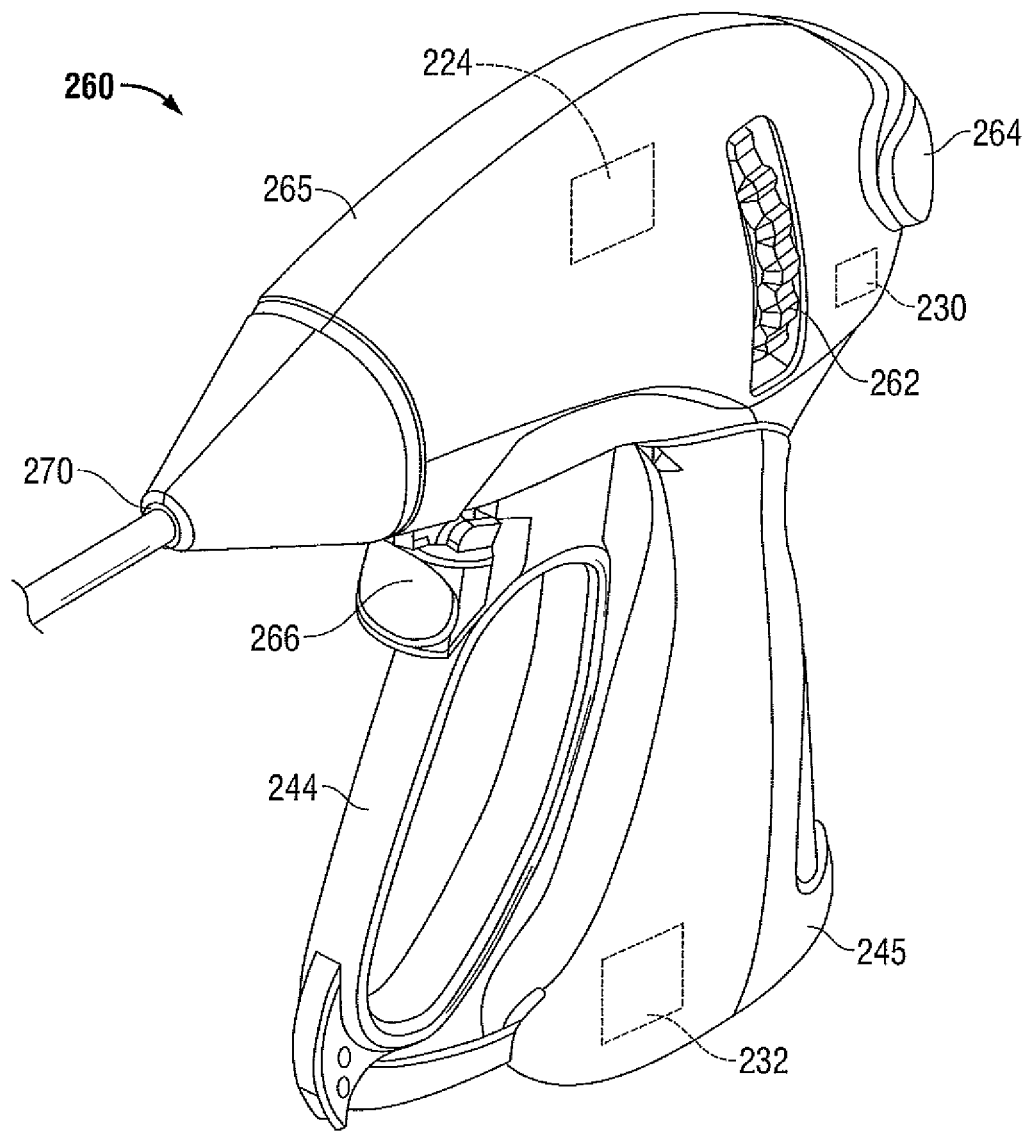

FIGS. 2A-C show three possible embodiments of remote 200, however, other embodiments may be possible. FIG. 2A discloses a first embodiment of a remote 220 that is generally circular in shape with a triangular front that may interconnect with the base 300 of the RC electrosurgical instrument 10. The circular shape allows the remote 220 to fit into the palm of the surgeon's M hand, where the surgeon M can rotate his/her wrist to move the tool in a corresponding manner by easily pushing one or more buttons 225, 227, 229, 231. The remote 220 includes at least one momentum sensor 224 and an infrared sensor 222. The remote may be configured with one or more buttons 225, 227, 229, 231 that may be located on the top, side, and/or bottom of the remote. Button 225 may be used to activate an electrical signal to coagulate or cut tissue, staple tissue, or perform other surgical functions. For example, button 227 may be used to move the end effector assembly 100 in very small increments. Additionally, the remote 220 includes a haptic feedback mechanism 232 that provides feedback about position, force used, instruction, and other similar uses. In an alternative embodiment, visual communication may be used to identify which instrument the remote is operating, problems with where the RC instrument 10 is located, battery life of remote, which remote in a master/slave relationship is controlling the instrument, and other problems with the RC instrument 10 or system. Alternatively, the remote 220 can be configured with audio feedback (not shown) to inform the surgeon M of problems or pre-recorded specific instrument functions. The remote 220 further includes data ports 226a and 226b for communicating with the instrument base 300. The data ports 226a and 226b may be connected directly to the instrument base 300 or wirelessly connected.

FIG. 2B discloses a second embodiment of a remote 240 for use with the remote controlled surgical system 100. Similar to the remote 220 in FIG. 2A, the remote 240 includes data ports 226a and 226b, momentum sensor 224, infrared sensor 222, and/or haptic feedback mechanism 232. Remote 240 is shaped with a handle 245 and a trigger 244. The trigger 244 is similar to button 225 on remote 220, and may be used to activate an electrical signal to coagulate or cut tissue, staple tissue, or perform another surgical function. Remote 240 further includes buttons 227, 229, and 231 used to perform other functions of the RC instrument 10. The size and shape of the handle 245 can be ergonomically shaped for a right-handed or left-handed surgeon and/or based on the size of the surgeon's hand.

FIG. 2C discloses a third embodiment of a remote 260. Similar to the remote 240 in FIG. 2B, the third remote 260 may include a housing 265, a momentum sensor 224, haptic feedback mechanism 232, handle 245, and/or trigger 244. Trigger 244 is similar to button 225 on remote 220, and may be used to activate an electrical signal to coagulate or cut tissue, staple tissue, or other procedure. Rotating wheel 262 is similar to button 227 on the first remote, and may be used to move the end effector assembly 100 in very small increments. Data port 230 wirelessly connects remote control 260 with the base 300 (see FIG. 3) of the RC electrosurgical instrument 10. Similar to the second remote 240, the size and shape of the handle 245 can be ergonomically shaped for a right-handed or left-handed surgeon and/or based on the size of the surgeon's hand. In alternative embodiments, remote 260 may also include opening 270 defined therein, where a surgeon M can insert the same type end effector assembly 100 and shaft 12 as used within the patient P during surgery. This would allow the surgeon or others the ability see how the end effector is moving.

Figure 3:
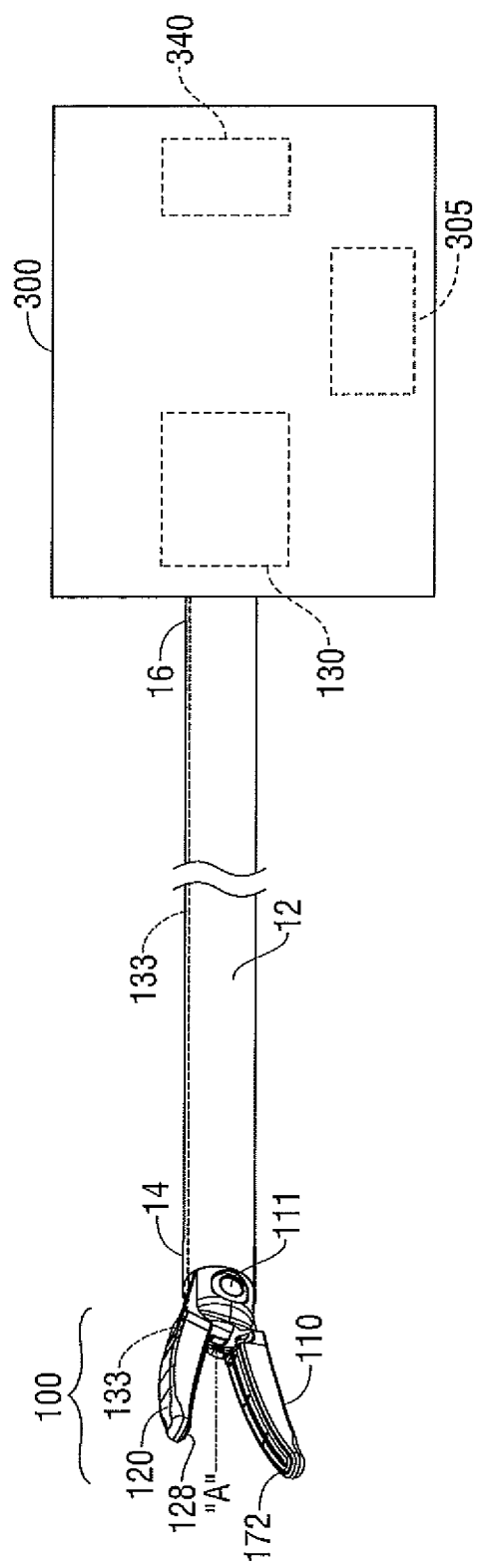
FIG. 3 is a perspective view of a remote controlled electrosurgical instrument in accordance with an embodiment of the present disclosure.

Referring to FIG. 3, a RC surgical instrument 10, such as forceps, includes a shaft 12 that has a distal end 14 configured to mechanically engage an end effector assembly 100 operably associated with the forceps 10 and a proximal end 16 that mechanically engages the base 300. In the drawings and in the descriptions that follow, the term "proximal," as is traditional, will refer to the end of the forceps 10 which is closer to a base 300, while the term "distal" will refer to the end that is farther from the base. Alternatively, the system may be used with a remote controlled pencil or other electrosurgical instrument.

Drive assembly 130 is in operative communication with the remote 200 through data port 340 for imparting movement of one or both of a pair of jaw members 110, 120 of end effector assembly 100. The drive assembly 130 may include a compression spring (not shown) or a drive wire 133 to facilitate closing the jaw members 110 and 120 around pivot pin 111. Drive wire 133 is configured such that proximal movement thereof causes one movable jaw member, e.g., jaw member 120, and operative components associated therewith, e.g., a seal plate 128, to move toward the other jaw member, e.g., jaw member 110. With this purpose in mind, drive rod or wire 133 may be made from any suitable material and is proportioned to translate within the shaft 12. In the illustrated embodiments, drive wire 133 extends through the shaft 12 past the distal end 14. Both jaw members 110 and 120 may also be configured to move in a bilateral fashion.

Base 300 receives an electrical signal from a generator (not shown). Generator may be connected to base 300 by a cable (not shown). By not including the generator within base 300, the size of base 300 may be smaller. Additionally, base 300 may be used with an existing generator system. Alternatively, generator may be part of base 300.

Remote control 200 (See FIG. 3A) may be in operative communication with an ultrasonic transducer (not shown) via data port 340 when the RC surgical instrument 10 is an ultrasonic instrument (not shown). Alternatively, base 300 may be arranged with multiple RC surgical instruments 10 attached. Each RC surgical instrument 10 may be removable or permanently attached to base 300.

Figure 4:
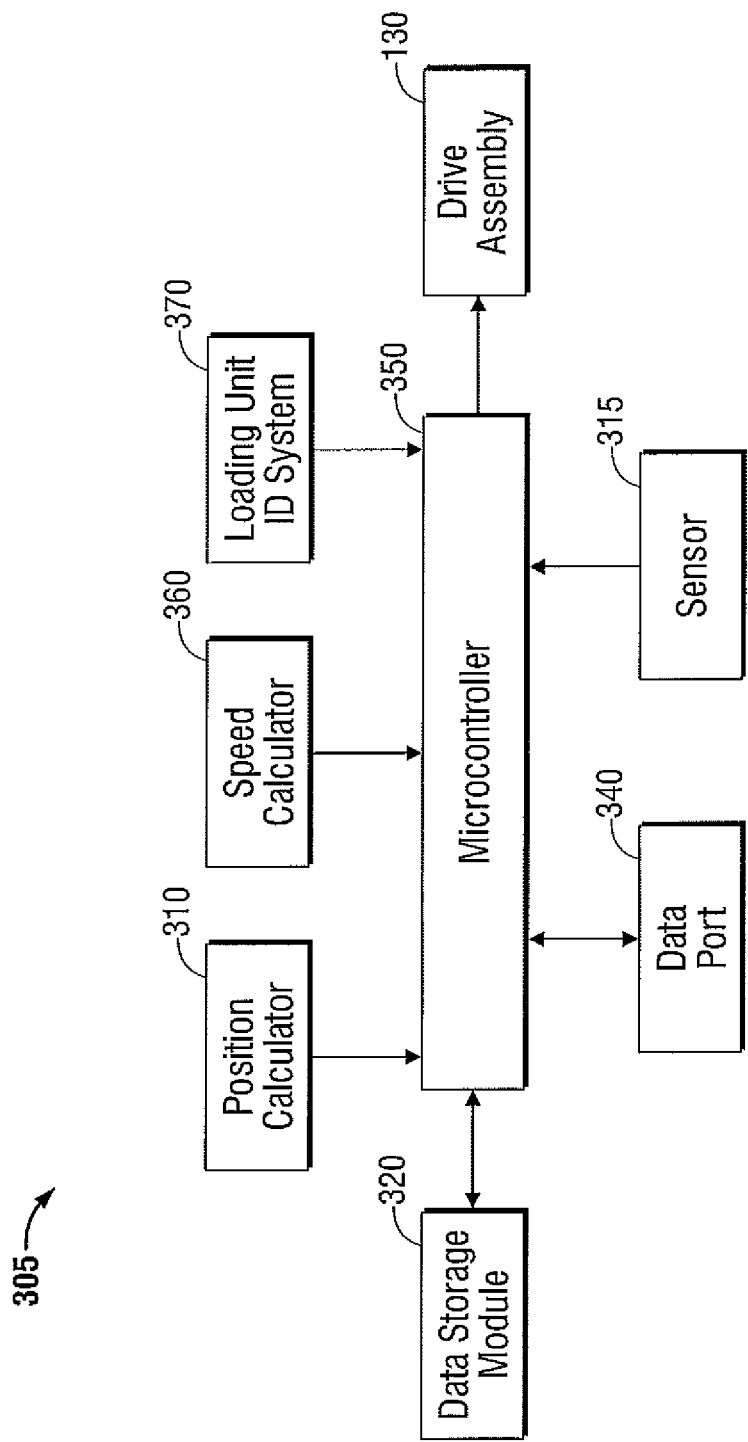
FIG. 4 is a schematic diagram of an electrosurgical instrument control system in accordance with an embodiment of the present disclosure.

FIG. 4 illustrates a control system 305 for the RC surgical instrument 10 including the microcontroller 350 which is coupled to the position and speed calculators 310 and 360, the loading unit identification system 370, the drive assembly 130, and a data storage module 340. In addition, the microcontroller 350 may be directly coupled to a sensor 315, such as a motion sensor, torque meter, ohm meter, load cell, current sensor, etc. The microcontroller 350 includes internal memory which stores one or more software applications (e.g., firmware) for controlling the operation and functionality of the RC surgical instrument 10.

The loading unit identification system 370 identifies to the microcontroller 350 which end effector assembly 100 is attached to the distal end 14 of the RC instrument 10. In an embodiment, the control system 300 is capable of storing information relating to the force applied by the end effector assembly 100, such that when a specific end effector assembly 100 is identified the microcontroller 350 automatically selects the operating parameters for the RC surgical instrument 10. For example, torque parameters could be stored in data storage module 320 for a laparoscopic grasper.

The microcontroller 350 also analyzes the calculations from the position and speed calculators 310 and 360 and other sensors 315 to determine the actual position, direction of motion, and/or operating status of components of the RC surgical instrument 10. The analysis may include interpretation of the sensed feedback signal from the calculators 310 and 360 to control the movement of the drive assembly 130 and other components of the RC surgical instrument 10 in response to the sensed signal. Alternatively, the location of the RC surgical instrument 10 may be calculated using the method disclosed in U.S. Ser. No. 12/720,881, entitled "System and Method for Determining Proximity Relative to a Critical Structure" filed on Mar. 10, 2010, which is hereby incorporated by reference. The microcontroller 350 is configured to limit the travel of the end effector assembly 100 once the end effector assembly 100 has moved beyond a predetermined point as reported by the position calculator 310. Specifically, if the microcontroller determines that the position of the end effector assembly 100 is within a safety zone determined by the AR controller 200, the microcontroller is configured to stop the drive assembly 130.

In one embodiment, the RC surgical instrument 10 includes various sensors 315 configured to measure current (e.g., an ampmeter), resistance (e.g., an ohm meter), and force (e.g., torque meters and load cells) to determine loading conditions on the end effector assembly 100. During operation of the RC surgical instrument 10 it is desirable to know the amount of force exerted on the tissue for a given end effector assembly 100. Detection of abnormal loads (e.g., outside a predetermined load range) indicates a problem with the RC surgical instrument 10 and/or clamped tissue which is communicated to the user.

The data storage module 320 records the data from the sensors 315 coupled to the microcontroller 350. In addition, the data storage module 320 may record the identifying code of the end effector assembly 100, user of surgical tool, and other information relating to the status of components of the RC surgical instrument 10. The data storage module 320 is also configured to connect to an external device such as a personal computer, a PDA, a smartphone, or a storage device (e.g., a Secure Digital™ card, a CompactFlash card, or a Memory Stick™) through a wireless or wired data port 340. This allows the data storage module 320 to transmit performance data to the external device for subsequent analysis and/or storage. The data port 340 also allows for "in the field" upgrades of the firmware of the microcontroller 350.

Figure 5:
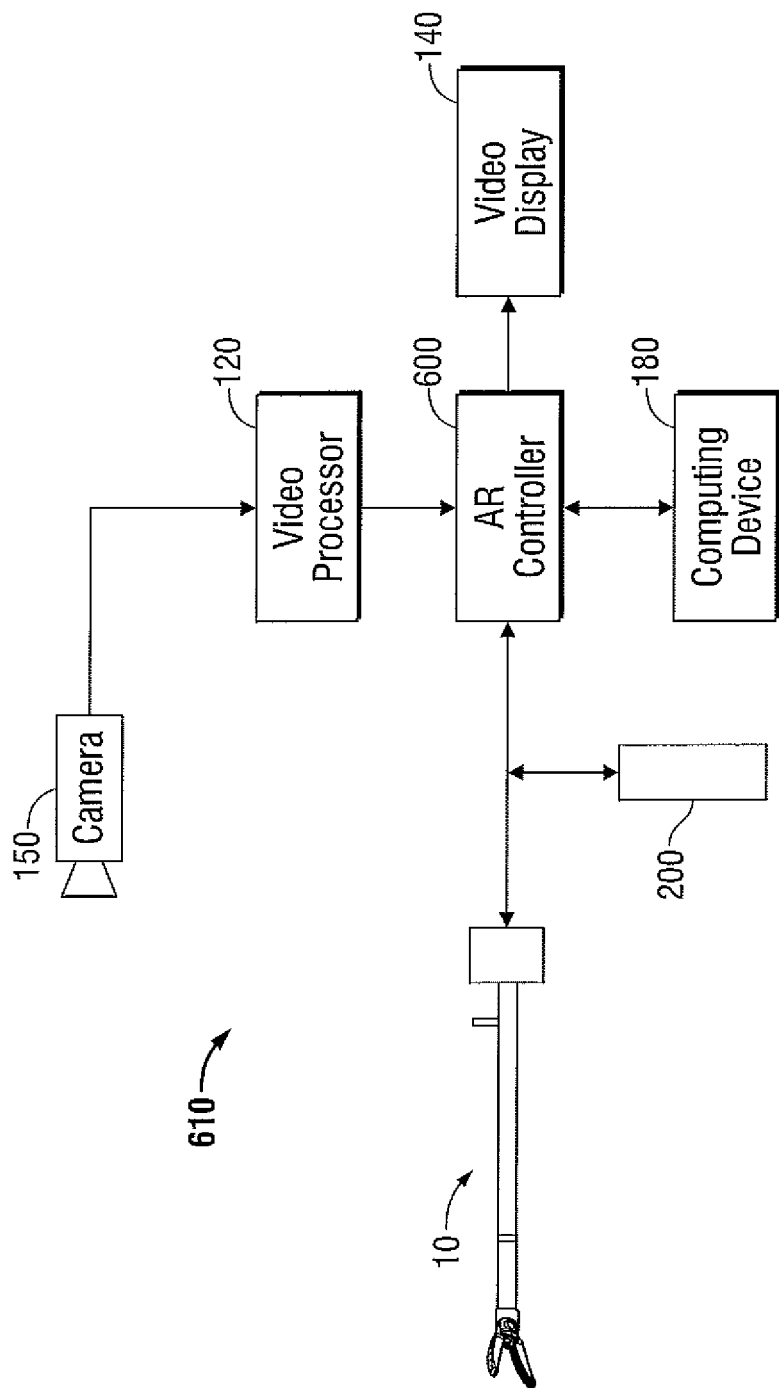
FIG. 5 is a schematic diagram of an augmented controller system in accordance with an embodiment of the present disclosure.
Figure 6:
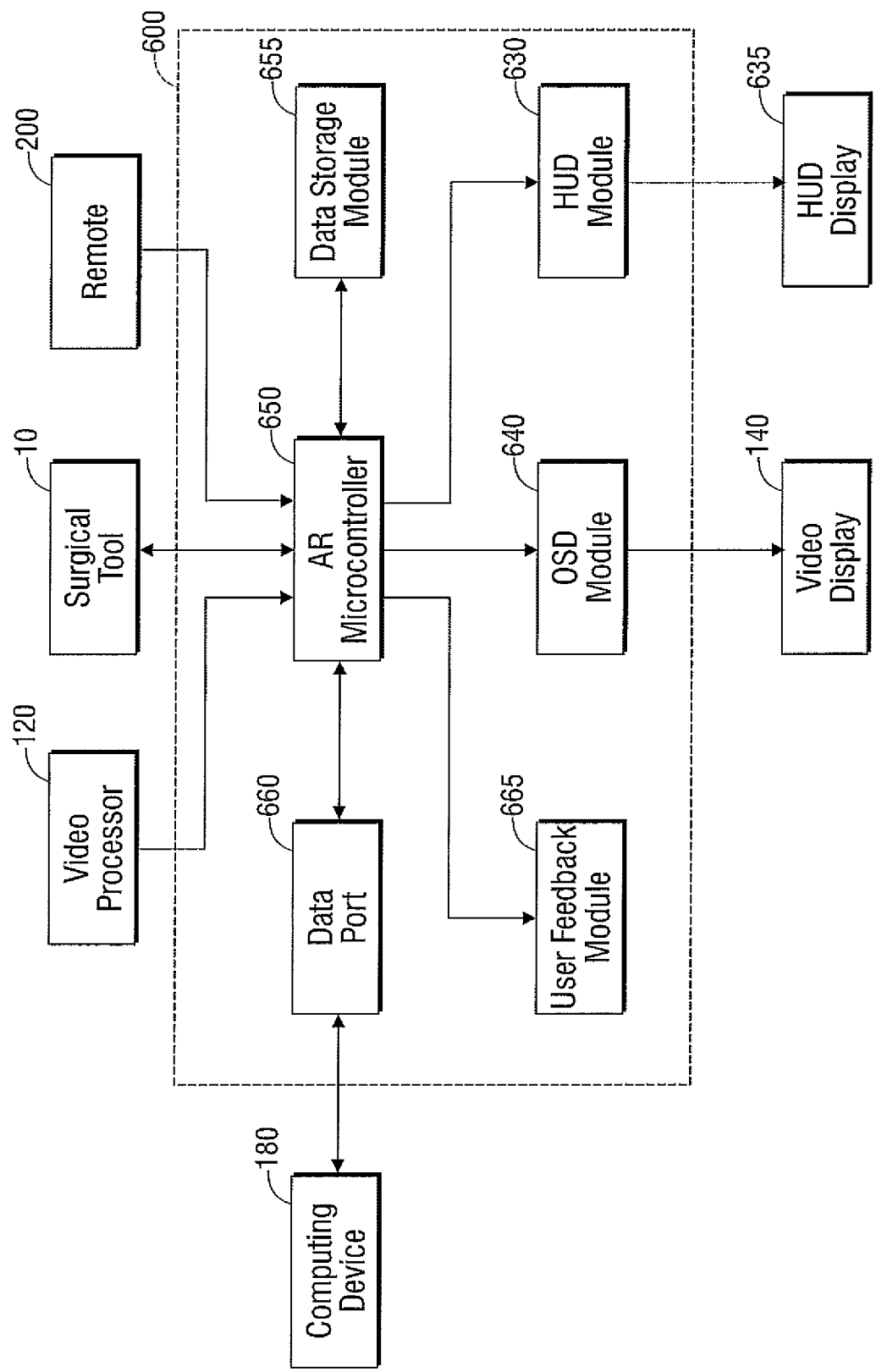
FIG. 6 is a schematic diagram of an augmented controller system in accordance with an embodiment of the present disclosure.

Embodiments of the present disclosure may include an augmented reality (AR) control system 610 as shown in FIGS. 5-6. The RC surgical instrument 10 is connected to an AR controller 600 via the data port 660 which may be either wired (e.g., FireWire, USB, Serial RS232, Serial RS485, USART, Ethernet, etc.) or wireless (e.g., Bluetooth®, ANT3®, KNX®, Z-Wave X10®, Wireless USB®, Wi-Fi, IrDA®, nanoNET®, TinyOS®, ZigBee®, 802.11 IEEE, and other radio, infrared, UHF, VHF communications and the like). Additionally, remote 200 (220, 240, 260) is connected to the AR controller 600 via data port 660 which may be either wired (e.g., FireWire®, USB, Serial RS232, Serial RS485, USART, Ethernet, etc.) or wireless (e.g., Bluetooth®, ANT3®, KNX®, Z-Wave, X10®, Wireless USB®, Wi-Fi®, IrDA®, nanoNET®, TinyOS®, ZigBee®, 802.11 IEEE, and other radio, infrared, UHF, VHF communications and the like).

FIG. 5 illustrates a schematic diagram of an AR control system 610 in accordance with an embodiment of the present disclosure. With reference to FIG. 5, the augmented reality (AR) controller 600 is configured to store data transmitted to the controller 600 by a RC surgical instrument 10 and a remote 200 (220, 240, 260) as well as process and analyze the data. The RC surgical instrument 10 is a robotic instrument. The AR controller 600 is also connected to other devices, such as a video display 140, a video processor 120 and a computing device 180 (e.g., a personal computer, a PDA, a smartphone, a storage device, etc.). The video processor 120 may be used for processing output data generated by the AR controller 600 for output on the video display 140. Additionally, the video processor 120 may receive a real time video signal from a camera 150 inserted into the patient during the surgical procedure. The computing device 180 may be used for additional processing of the pre-operative imaged data. In one embodiment, the results of pre-operative imaging such as an ultrasound, MRI, x-ray, or other diagnosing image may be stored internally for later retrieval by the computing device 180.

The AR controller 600 includes a data port 660 (FIG. 6) coupled to the microcontroller 650 which allows the AR controller 600 to be connected to the computing device 180. The data port 660 may provide for wired and/or wireless communication with the computing device 180 providing for an interface between the computing device 180 and the AR controller 600 for retrieval of stored pre-operative imaging data, configuration of operating parameters of the AR controller 600 and upgrade of firmware and/or other software of the AR controller 600.

Components of the AR controller 600 are shown in FIG. 6. The AR controller 600 includes a microcontroller 650, a data storage module 655 a user feedback module 665, an OSD module 640, a HUD module 630, and a data port 660.

The data storage module 655 may include one or more internal and/or external storage devices, such as magnetic hard drives, or flash memory (e.g., Secure Digital® card, Compact Flash® card, or MemoryStick®). The data storage module 655 is used by the AR controller 600 to store data from the RC surgical instrument 10 and remote 200 (220, 240, 260) for later analysis of the data by the computing device 180. The data may include information supplied by a sensor 315 (FIG. 4), such as a motion sensor, torque sensor, and other sensors disposed within the RC surgical instrument 10.

The microcontroller 650 may supplant, complement, or supplement the control circuitry 305 of the RC surgical instrument 10 shown in FIG. 4. The microcontroller 650 includes internal memory which stores one or more software applications (e.g., firmware) for controlling the operation and functionality of the RC surgical instrument 10. The microcontroller 650 processes input data from the computing device 180 and adjusts the operation of the RC surgical instrument 10 in response to the inputs. The RC surgical instrument 10 is configured to connect to the AR controller 600 wirelessly or through a wired connection via a data port 340. The microcontroller 650 is coupled to the user feedback module 665 which is configured to inform the user of operational parameters of the RC surgical instrument 10. The user feedback module 665 may be connected to a user interface. The user feedback module 665 may be coupled to the haptic mechanism 232 within the remote 200 (220, 240, 260) to provide for haptic or vibratory feedback. The haptic feedback may be used in conjunction with the auditory and visual feedback or in lieu of the same to avoid confusion with the operating room equipment which relies on audio and visual feedback. The haptic mechanism 232 may be an asynchronous motor that vibrates in a pulsating manner. In one embodiment, the vibrations are at a frequency of about 30 Hz or above. The haptic feedback can be increased or decreased in intensity. For example, the intensity of the feedback may be used to indicate that the forces on the instrument are becoming excessive. In alternative embodiments, the user feedback module 265 may also include visual and/or audible outputs.

The microcontroller 650 outputs data on video display 140 and/or the heads-up display (HUD) 635. The video display 140 may be any type of display such as an LCD screen, a plasma screen, electroluminescent screen and the like. In one embodiment, the video display 140 may include a touch screen and may incorporate resistive, surface wave, capacitive, infrared, strain gauge, optical, dispersive signal or acoustic pulse recognition touch screen technologies. The touch screen may be used to allow the user to provide input data while viewing AR video. For example, a user may add a label identifying the surgeon for each tool on the screen. The HUD display 635 may be projected onto any surface visible to the user during surgical procedures, such as lenses of a pair of glasses and/or goggles, a face shield, and the like. This allows the user to visualize vital AR information from the AR controller 600 without loosing focus on the procedure.

The AR controller 600 includes an on-screen display (OSD) module 640 and a HUD module 630. The modules 640, 630 process the output of the microcontroller 650 for display on the respective displays 140 and 635. More specifically, the OSD module 640 overlays text and/or graphical information from the AR controller 600 over video images received from the surgical site via camera 150 (FIG. 1) disposed therein. Specifically, the overlaid text and/or graphical information from the AR controller 600 includes computed data from pre-operative images, such as x-rays, ultrasounds, MRIs, and/or other diagnosing images. The computing devices 180 stores the one or more pre-operative images. In an alternative embodiment, the data storage module 655 can store the pre-operative image. The AR controller 600 processes the one or more pre-operative images to determine margins and location of an anatomical body in a patient, such as an organ or a tumor. Alternatively, the computing device 180 can process and analyze the pre-operative image. Additionally, the AR controller can create safety boundaries around delicate structures, such as an artery or organ. Further, the AR controller 600 can decipher the one or more pre-operative images to define structures, organs, anatomical geometries, vessels, tissue planes, orientation, and other similar information. The AR controller 600 overlays the information processed from the one or more pre-operative images onto a real time video signal from the camera 150 within the patient. The augmented video signal including the overlaid information is transmitted to the video display 140 allowing the user to visualize more information about the surgical site including area outside the vision of the camera 150. Additionally, as the camera moves around the surgical site, the labels and/or data overlaid is moved to the appropriate location on the real time video signal.

Figure 7:
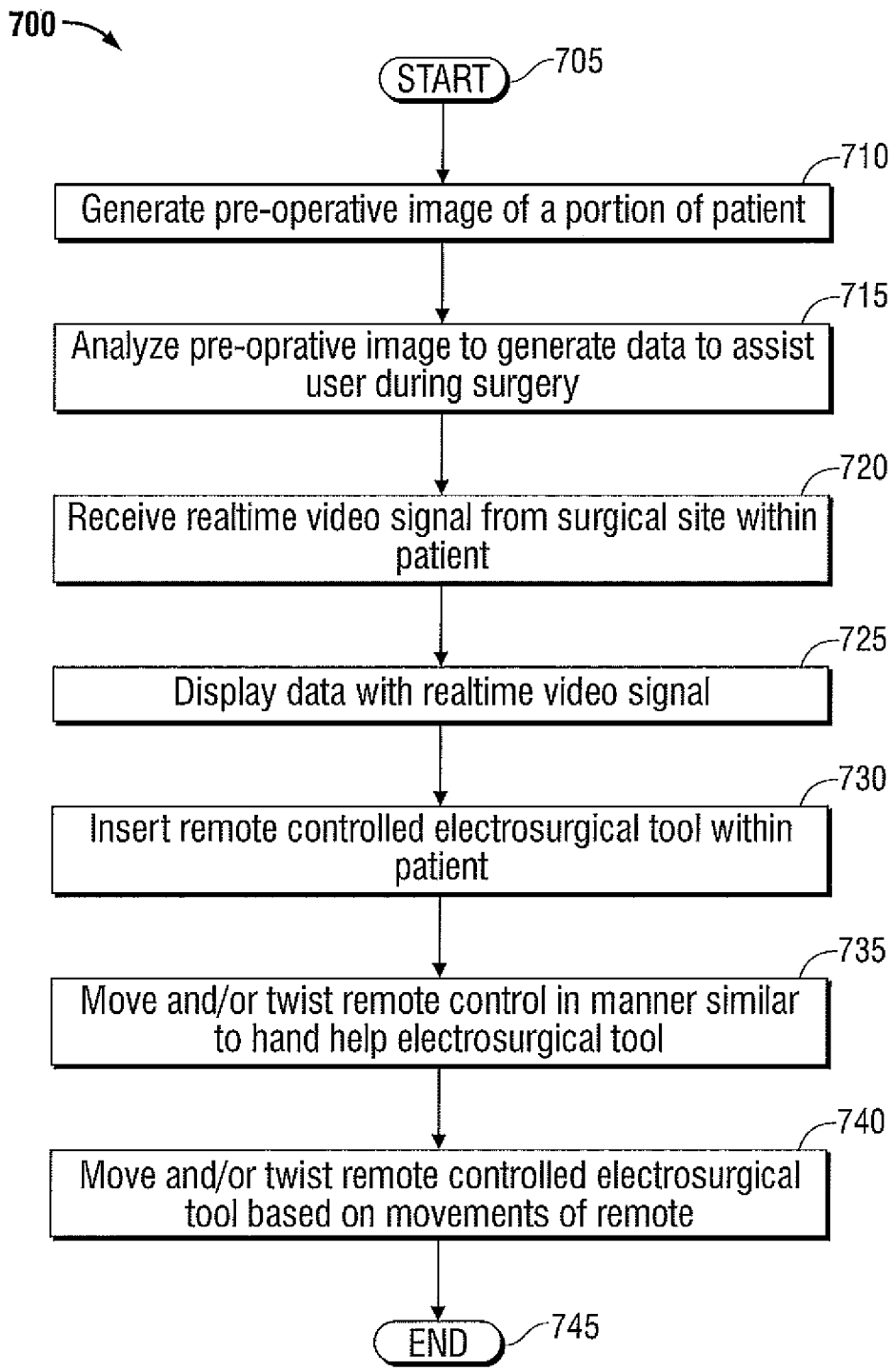
FIG. 7 is a flow diagram of a process for controlling an electrosurgical instrument with a remote in accordance with an embodiment of the present disclosure.

FIG. 7 is a flow diagram of a process 700 for controlling an electrosurgical instrument with a remote 200 (220, 240, 260) according to an embodiment of the invention. After the process 700 starts at step 705, a pre-operative image is generated from a diagnosing imaging source, such as from an MRI, ultrasound, x-ray, CAT scan, etc. at step 710. The pre-operative image is taken of an anatomical section of the patient, which may include organs, tissue, vessels, bones, tumors, muscles, etc. Multiple images can be generated from one or more sources based on the information required by the surgeon M. Next, the pre-operative image is analyzed to generate data to assist the surgeon M during surgery at step 715. The analyzing may be done by the computing device 180 or the microprocessor 650. The data may include margins and location of the anatomical section. Prior to starting the surgery, a camera 150 is inserted within the patient. A real time video signal of the patient during the surgical procedure is received at AR controller 600 during the surgical procedure at step 720. The analyzed data is displayed with the real time video signal at step 725. For example, if the anatomical section is a tumor then the location and margins of the tumor are calculated and then the name and margins are augmented onto the video signal to assist the surgeon M in locating the tumor. A RC electrosurgical instrument 10 is inserted into a body cavity or incision at step 730. A user M moves, twists, and/or selects buttons on the remote control 200 at step 735. The surgeon M may move the remote 200 in a manner similar to actions done with a handheld electrosurgical instrument. Before the process 700 ends at step 745, the RC surgical instrument 10 moves, twist, and/or performs other action based on the movements performed by the remote 200 at step 740. The movements of the remote 200 are sent wirelessly or the remote is directly connected to the RC surgical instrument 10.

Figure 8:
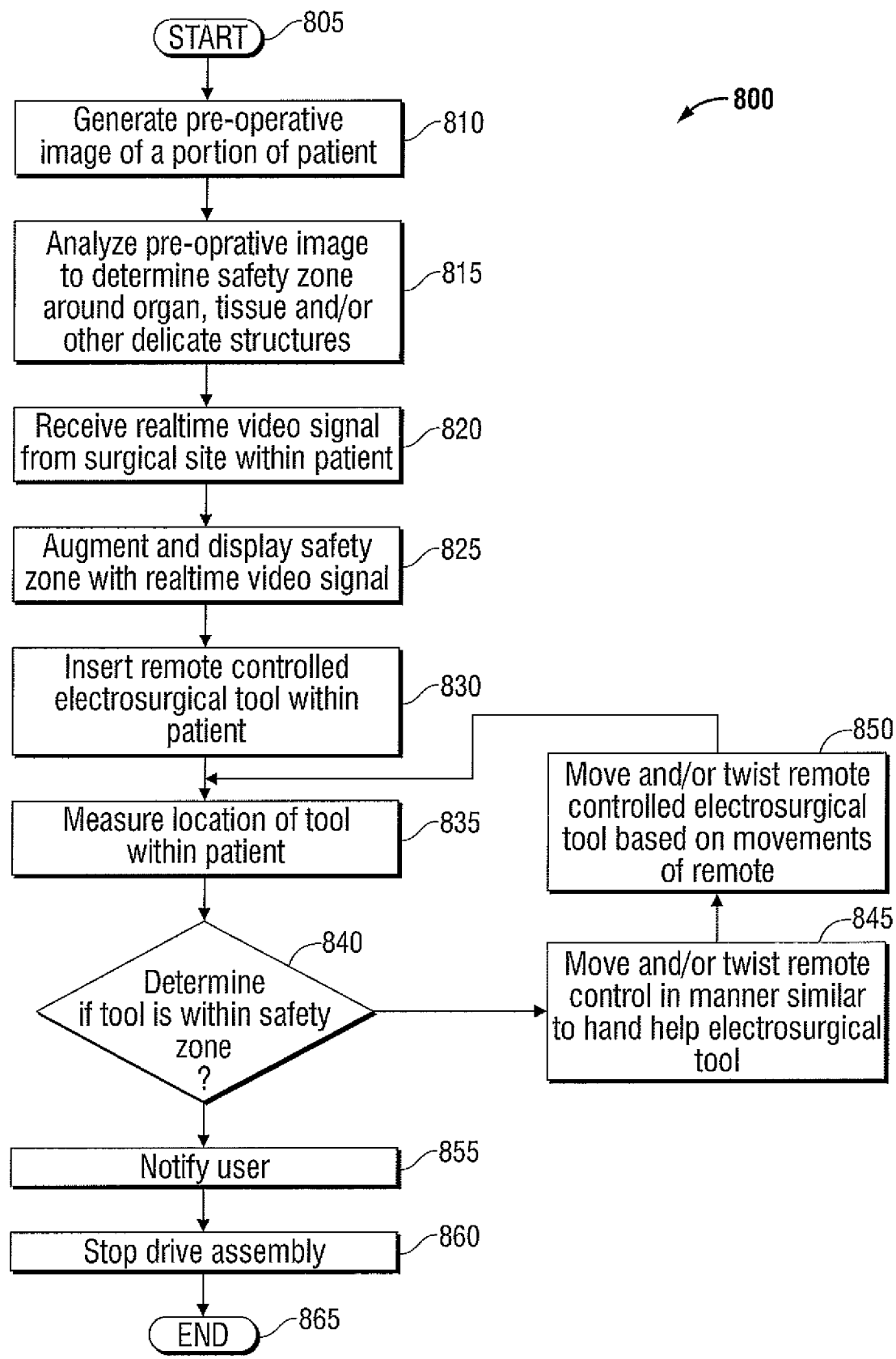
FIG. 8 is a flow diagram of a process for determining if the remote controlled electrosurgical instrument is within an augmented safety zone in accordance with an embodiment of the present disclosure.

FIG. 8 is a flow diagram of process 800 for determining if the remote controlled electrosurgical instrument is within an augmented safety zone according to an embodiment of the invention. After the process 800 starts at step 805, a pre-operative image of an anatomical section of a patient is generated at step 810. The pre-operative image can be generated from any type of diagnosing image, such as an x-ray, MRI, CAT scan, ultrasound, etc. The pre-operative image analyzed to determine a safety zone around organs, tissue, and/or other delicate anatomical structures at step 815. Prior to starting the surgical procedure, a camera 150 is inserted within the patient. During the surgical procedure, a real time video signal is received by the AR controller 600 via video processor 120 at step 825. The AR controller 600 augments the safety zone onto the video signal at step 830. For example, the safety zone may be represented as a cross hatched area or in a different color, such as a yellow area around an organ. A RC electrosurgical instrument 10 is inserted into a cavity or incision 15 within the patient P at step 830. The location of the surgical instrument 10 within the patient is measured at step 835 using the position calculator 310, speed calculator 360, and other sensors 315. Alternatively, the location of the RC instrument 10 and/or end effector assembly 100 may be calculated using the method disclosed in U.S. Ser. No. 12/720,881, entitled "System and Method for Determining Proximity Relative to a Critical Structure" filed on Mar. 10, 2010, which is hereby incorporated by reference. The AR controller 200 determines if the RC surgical instrument 10 is within the safety zone at step 840. If the RC surgical instrument 10 is not within the safety zone, then allow the surgeon M to move, twist, and/or select buttons on remote 200 at step 845. The movement of the remote may be similar to movement of a handheld electrosurgical instrument. The RC electrosurgical instrument 10 then moves, twists, and/or performs action based on the movement or actions from the remote at step 850. Then, the system measures the new location of the RC electrosurgical instrument 10 at step 835. If the RC electrosurgical instrument 10 is within the safety zone, then the AR controller 600 notifies the surgeon at step 855. This notification can be visual, audible, or haptic feedback. Additionally, before process 800 ends at step 865, the AR controller 600, if necessary, can stop the drive assembly 130 at step 860.

Figure 9:
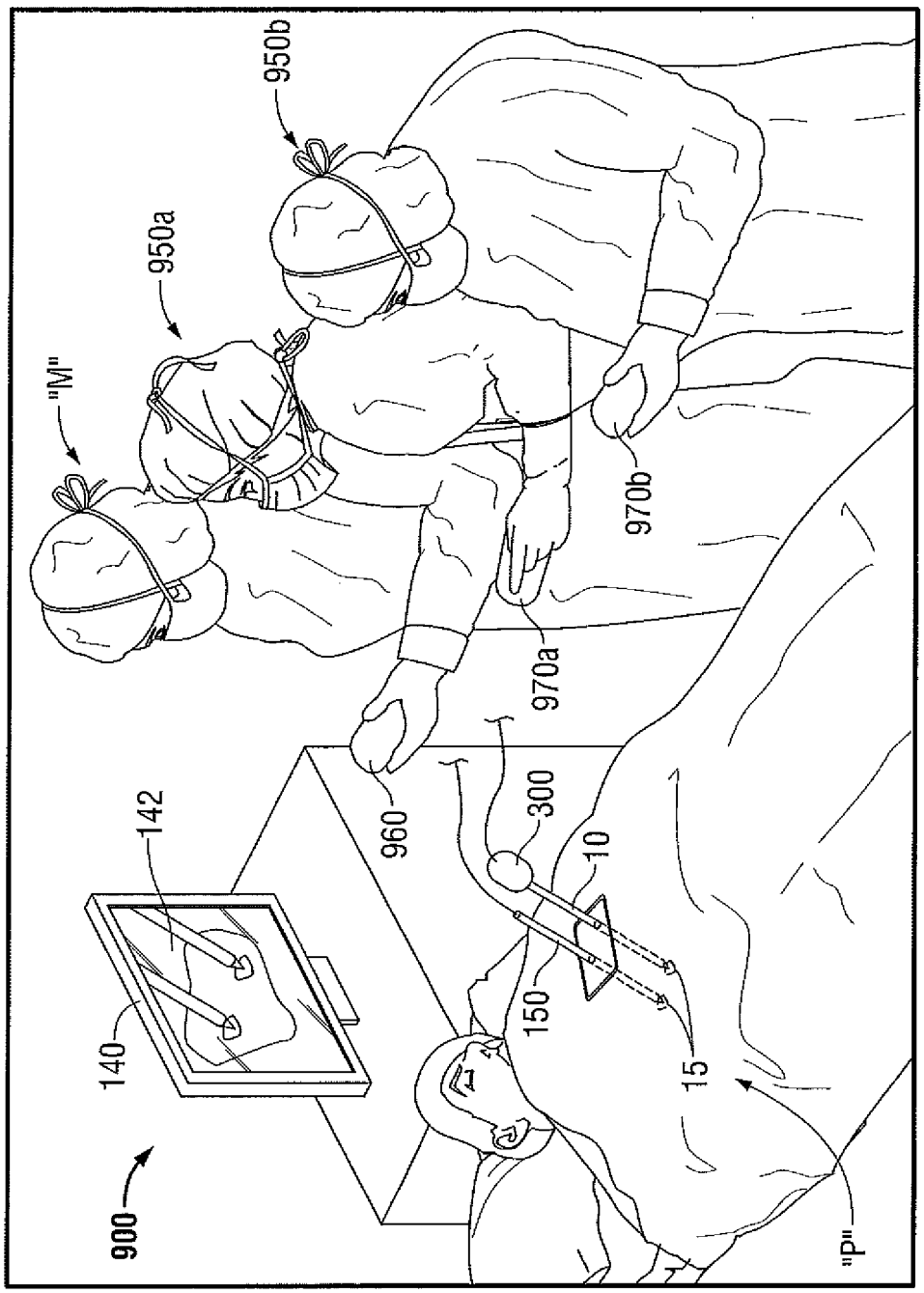
FIG. 9 is a schematic diagram of a master/slave remote system in accordance with an embodiment of the present disclosure.

FIG. 9 illustrates a schematic diagram of a master/slave remote control system 900 according to an embodiment of the invention. Similar to the remote controlled surgical system 100 shown in FIG. 1, the master/slave remote control system 900 includes a patient P with at least one incision 15, a RC electrosurgical instrument 10, a base 300, a camera 150, and a display 140 with an augmented displayed image 142. Additionally, the master/slave remote control system 900 includes a first user that is the master M (surgeon) that uses a master remote 960 and at least one slave user 950*a*, 950*b* that uses a slave remote 970*a, b*. As the master M moves, tilts, selects buttons on the master remote 960, the slave remote may receive haptic feedback to teach the slave user how to move the slave remote 970*a*. Additionally, the master remote 960 may allow the master M to transfer control to slave remote 970*a* and then to 970*b* or back to the master remote 960. The master M can be located in the same room with slave 950*a* and/or 950*b* or the master M can be located in a remote location, such as another state or country.

Figure 10:
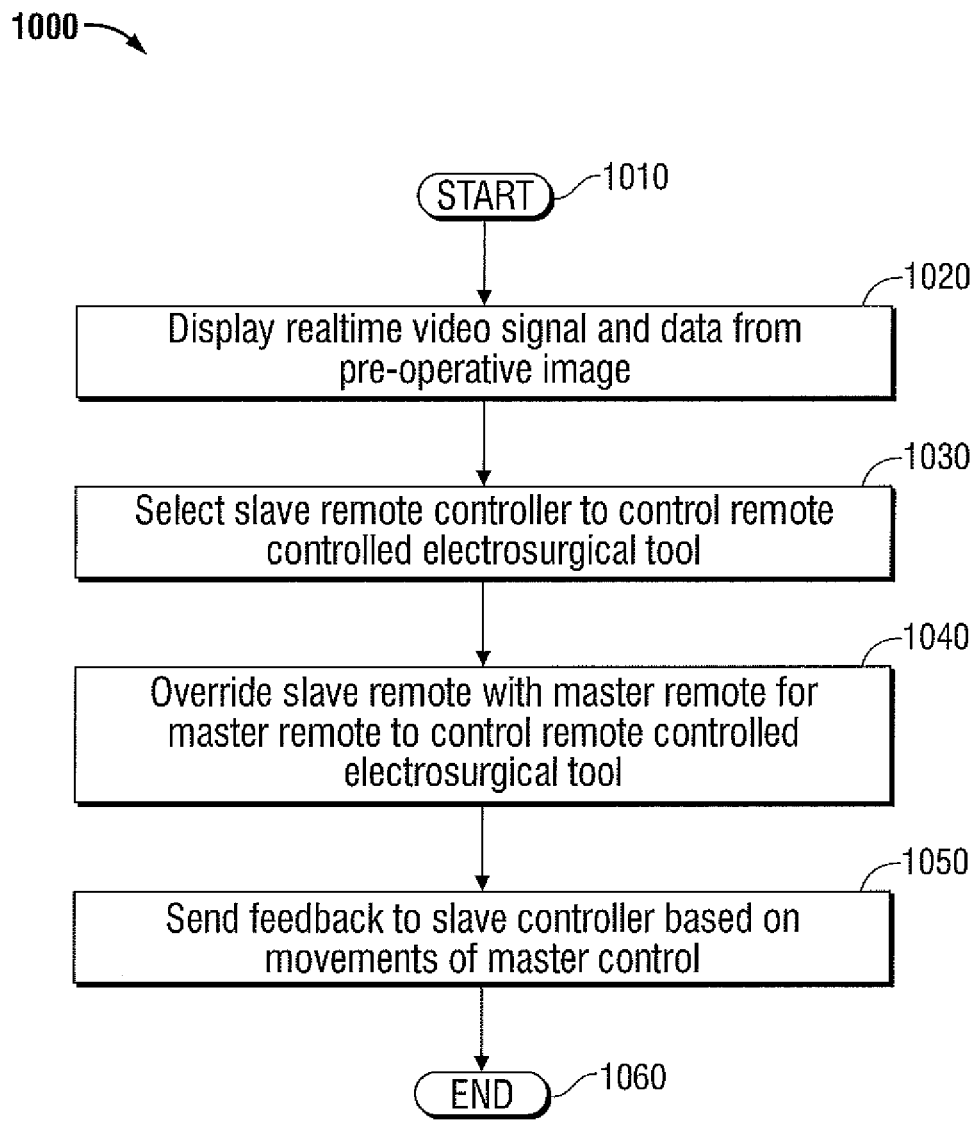
FIG. 10 is a flow diagram of a process for sharing control of an electrosurgical instrument between master and slave remotes in accordance with an embodiment of the present disclosure.

FIG. 10 is a flow diagram of a process 1000 for sharing control of an electrosurgical instrument between a master and a slave according to an embodiment of the invention. The process 1000 starts at step 1010, displaying a real time video signal with data from a pre-operative image at step 1020. The master remote 960 selects a slave remote 970*a* to control the RC electrosurgical instrument at step 1030. The slave user 950*a* moves, twists, or selects buttons on the slave remote 970*a* to control the RC electrosurgical instrument 10. The master M may override the slave remote 970*a* to regain control of the RC electrosurgical instrument at step 1040.

Before the process 1000 ends at step 1060, the master M moves, tilts, and/or selects buttons on the master remote 960, haptic feedback is sent to the slave remote 970*a*, *b* at step 1050 to train the slave user 950*a*, *b* how to use the remote.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing a surgical procedure, the method comprising:
   using a remote-controlled surgical instrument as a hand-held instrument to perform a surgical task while a wireless remote is mechanically connected to the remote-controlled surgical instrument;
   using the wireless remote to perform a surgical task when the wireless remote is free from mechanical contact with the remote-controlled surgical instrument; and
   mechanically connecting the wireless remote with the remote-controlled surgical instrument such that the wireless remote is in physical contact with the remote-controlled surgical instrument.

2. The method according to claim 1, further comprising selecting a second remote-controlled surgical instrument using a user interface on the wireless remote.

3. The method according to claim 1, further comprising transferring control of the remote-controlled surgical instrument from the wireless remote to a slave remote.

4. The method according to claim 3, further comprising utilizing the wireless remote to transfer control of the remote-controlled surgical instrument from the slave remote to the wireless remote.

5. The method according to claim 3, further comprising sending feedback to the slave remote based on at least one of movements or actions of the wireless remote.

6. The method according to claim 1, further comprising tracking movement of the wireless remote with at least one momentum sensor of the wireless remote.

7. The method according to claim 1, further comprising using at least one infrared sensor on the wireless remote to facilitate mechanically connecting the wireless remote with the remote-controlled surgical instrument.

8. The method according to claim 1, further comprising tracking movement of the wireless remote along x-, y- and z-axes using at least three momentum sensors of the wireless remote.

9. The method according to claim 1, further comprising selecting a feature on the wireless remote to activate at least one of a clamping function of the remote-controlled surgical instrument, radio frequency energy for coagulation or cutting, or a stapling function of the remote-controlled surgical instrument.

10. The method according to claim 1, further comprising mechanically engaging the remote-controlled surgical instrument with at least one data port disposed at a distal position of the wireless remote when the wireless remote is mechanically connected with the remote-controlled surgical instrument.

11. The method according to claim 1, further comprising communicating data from the wireless remote to the remote-controlled surgical instrument.

12. A method of performing a surgical procedure, the method comprising:
    using a remote-controlled surgical instrument as a hand-held instrument to perform a surgical task while a wireless remote is mechanically connected to the remote-controlled surgical instrument;
    using the wireless remote to perform a surgical task when the wireless remote is free from mechanical contact with the remote-controlled surgical instrument; and
    selecting a second remote-controlled surgical instrument using a user interface on the wireless remote.

13. A method of performing a surgical procedure, the method comprising:
    using a remote-controlled surgical instrument as a hand-held instrument to perform a surgical task while a wireless remote is mechanically connected to the remote-controlled surgical instrument;
    using the wireless remote to perform a surgical task when the wireless remote is free from mechanical contact with the remote-controlled surgical instrument; and
    mechanically engaging the remote-controlled surgical instrument with at least one data port disposed at a distal position of the wireless remote when the wireless remote is mechanically connected with the remote-controlled surgical instrument.

* * * * *